United States Patent [19]

Scheller et al.

[11] Patent Number: 4,757,426
[45] Date of Patent: Jul. 12, 1988

[54] ILLUMINATION SYSTEM FOR FIBER OPTIC LIGHTING INSTRUMENTS

[75] Inventors: Gregg D. Scheller, Ballwin; Kevin Klug, St. Louis; Richard Wendt, Des Peres; James Easley, Bridgeton, all of Mo.

[73] Assignee: Storz Instrument Company, St. Louis, Mo.

[21] Appl. No.: 927,827

[22] Filed: Nov. 6, 1986

[51] Int. Cl.⁴ .............................................. F21V 19/04
[52] U.S. Cl. ....................................... 362/20; 362/32; 362/250; 362/272; 362/284; 362/804
[58] Field of Search ................... 362/20, 32, 119, 233, 362/250, 254, 272, 284, 296, 804, 285, 286

[56] References Cited

U.S. PATENT DOCUMENTS

| | | | |
|---|---|---|---|
| 3,775,606 | 11/1973 | Bazell et al. | 362/32 |
| 4,061,911 | 12/1977 | Krasin | 362/20 |
| 4,356,534 | 10/1982 | Hattori | 362/285 |
| 4,608,622 | 8/1986 | Gonser | 362/32 |
| 4,623,217 | 11/1986 | Hallen | 362/32 |

FOREIGN PATENT DOCUMENTS

| | | | |
|---|---|---|---|
| 2657852 | 7/1977 | Fed. Rep. of Germany | 362/32 |
| 3207926 | 9/1983 | Fed. Rep. of Germany | 362/285 |

Primary Examiner—Charles J. Myhre
Assistant Examiner—David A. Okonsky
Attorney, Agent, or Firm—Harness, Dickey & Pierce

[57] ABSTRACT

The illumination system has primary and secondary light sources with a lamp current sensor control circuit for automatically switching from the primary lamp to the secondary lamp in the event the primary lamp fails. An illumination directing mirror is positioned between the light sources and directs one or the other of the light sources towards a fiber optic cable. The lamps are mounted on a movable carriage which is remotely controllable by a pneumatic cylinder. The carriage moves to alter the distance from the lamp to the port of the fiber optic cable. This controls the intensity of illumination entering the cable without changing the color temperature of the light.

20 Claims, 3 Drawing Sheets

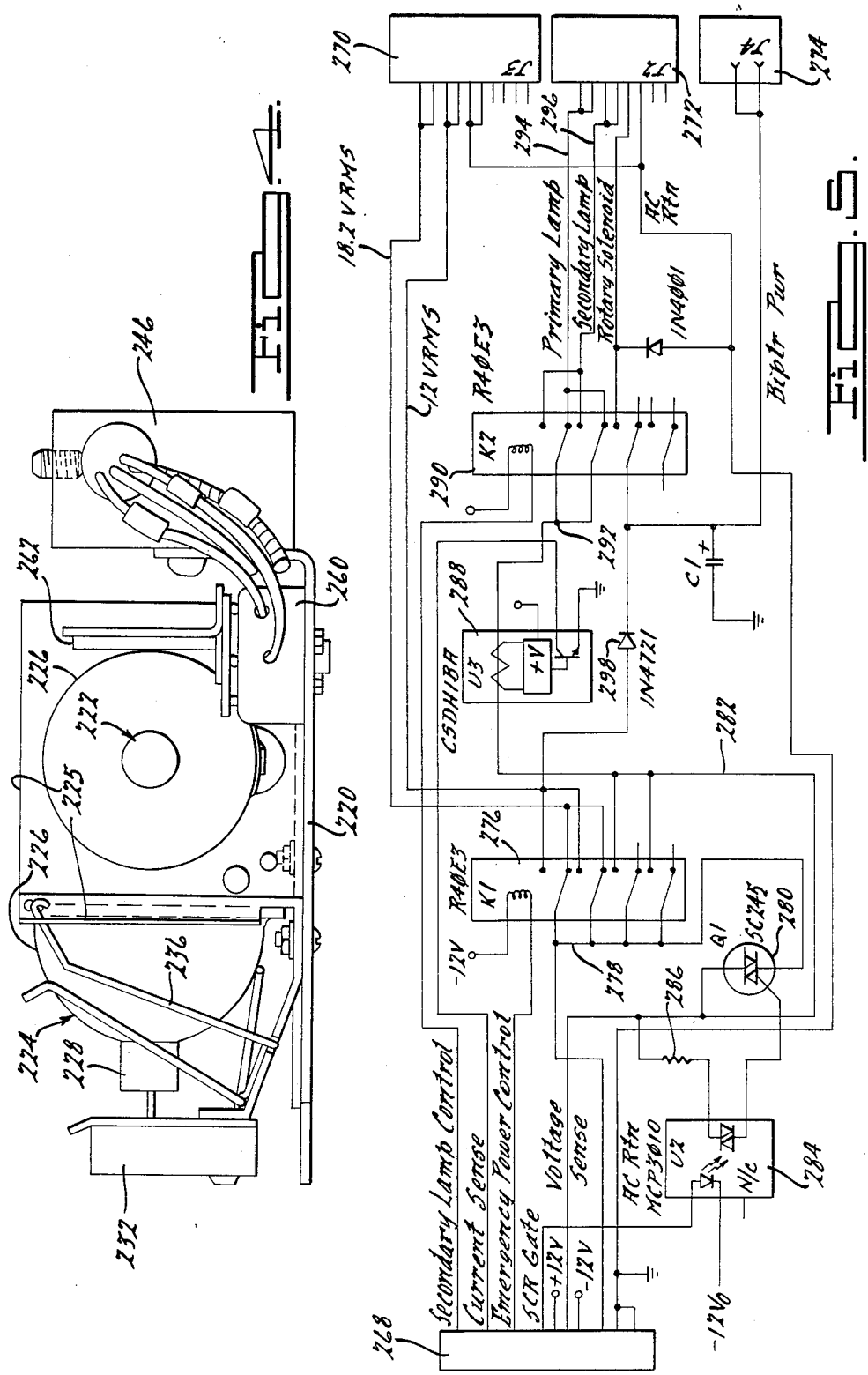

ILLUMINATION SYSTEM FOR FIBER OPTIC LIGHTING INSTRUMENTS

BACKGROUND AND SUMMARY OF THE INVENTION

The present invention relates generally to microsurgical and opthalmic systems and more particularly to an illumination system for providing controlled intensity light at the surgical situs.

In microsurgical systems, such as ophthalmic systems and vitrectomy systems, it is common to provide a source of illumination which can be coupled to a fiber optic cable or to a fiber optic microsurgical illumination instrument, in order to provide light at the surgical situs during surgery. Fiber optic cables are often used for this purpose as they can be made very thin and flexible and are well adapted for inserting directly into the tissue or organ being operated on. Lamps with electronic dimmer circuits are frequently used as the source of illumination to which the fiber optic cable is optically connected.

There are at least two drawbacks with conventional microsurgical illumination systems of this type. One drawback is that, when dimming the lamp using an electronic dimmer circuit, the color temperature of the illumination changes, typically from a comparatively white light to an orange or red light as the light is dimmed. This change in color may be undesirable, since the color of the illuminated tissue or organ is often used for diagnostic purposes. Accordingly, the inability to maintain a constant color temperature illumination is a drawback with conventional illumination systems.

Another drawback is encountered when the lamp fails during surgery. Conventional systems make provisions for this possibility by employing an auxiliary light source which can be manually turned on in the event of a primary light source failure. Commonly, the auxiliary light source is a separate light source with a separate optical coupler for attachment to the fiber optic cable. In order to use such a system, the fiber optic cable must be disconnected from the primary light source coupler and then reconnected to the auxiliary coupler, while at the same time the auxiliary light source must be turned on. Of course, this takes time to accomplish and requires the surgeons and nursing staff to be familiar with the auxiliary light source connection procedure and use.

Aside from the inconvenience, it is considered undesirable to disconnect the fiber optic cable from one optical coupler in order to connect it to the other during surgery, since the fiber optic cable is usually sterilized and the sterile field should not be broken by disconnecting the cable. Also, replacing the burned out lamp is not considered to be a viable alternative because it is time consuming and the bulb will still be quite hot. Additionally, replacement of a burned out lamp may be further complicated if the operating room has been darkened to facilitate a particular surgical procedure.

In order to overcome these drawbacks and to provide an improved illumination system for microsurgical uses, the present invention provides a movable multiple lamp system with an illumination directing mirror which operates automatically when the primary lamp fails. Current flow through the primary lamp is continually monitored so that changeover to the auxiliary lamp occurs quickly and automatically. The lamps are mounted on a movable carriage which may be remotely controlled to move the lamps toward and away from the optical coupler to which the fiber optic cable is attached. In this fashion, the intensity of the illumination supplied to the optical port of the optical coupler can be remotely controlled without the need to dim the lamps electrically. This ensures that the color temperature of the lamps remains substantially constant.

In summary, the invention comprises an illumination system for a microsurgical apparatus which comprises a base and a lamp carriage mounted on the base for movement relative to the base. A lamp or lamp system is carried on the lamp carriage for providing illumination and a fiber optic coupler is disposed on the base for coupling to a fiber optic microsurgical illumination instrument. The fiber optic coupler has an optical port positioned to receive illumination from the lamp or lamp system. A means is coupled to the carriage for moving the carriage selectively toward and away from the coupler to thereby control the intensity of the illumination entering the optical port. A pneumatic drive cylinder may be employed for this purpose and the carriage may be provided with at least one rail mounted on the base for assisting or confining movement of the carriage in a linear direction.

Further in accordance with the invention, there is provided an illumination system comprising at least two lamps supported on the carriage or base for providing illumination. The system further comprises an illumination controlling mechanism supported on the base for selectively causing the illumination from either of the lamps to illuminate the optical port. The illumination controlling mechanism includes an illumination directing means such as a mirror for selectively directing the illumination from either of the lamps towards the optical port. The controlling means is actuated by a mechanism for sensing when one of the lamps is not providing illumination; the mechanism operates by automatically causing the controlling means to cause the second lamp to illuminate the optical port. Preferably, the mirror is movable from a first position whereby a first one of the lamps illuminates the optical port, to a second position whereby a second one of the lamps illuminates the optical port. Failure of the first lamp is sensed by monitoring the electrical current flow through the lamp using a sensor, such as a Hall effect sensor. The lamps are preferably a constant color temperature lamp, such as a quartz halogen lamp of the type found in slide projectors.

For a more complete understanding of the invention and its objects and advantages, reference may be had to the following specification and to the accompanying drawings.

BRIEF DESCRIPTION OF THE DRAWINGS

FIG. 4 is a detailed view of the lamp and carriage assembly of the illumination system; and FIG. 5 is a schematic diagram of the lamp driver circuit of the invention.

DESCRIPTION OF THE PREFERRED EMBODIMENT

Figure 1:
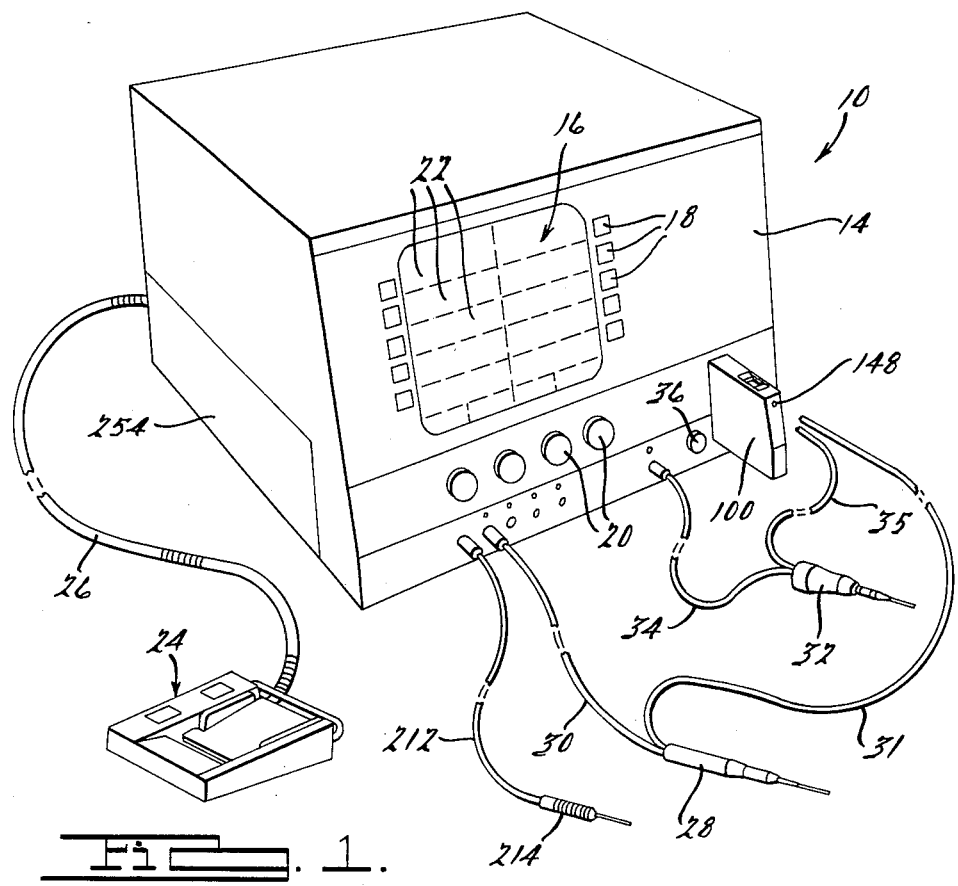
FIG. 1 is a perspective view of the microsurgical system of the invention.
Figure 2:
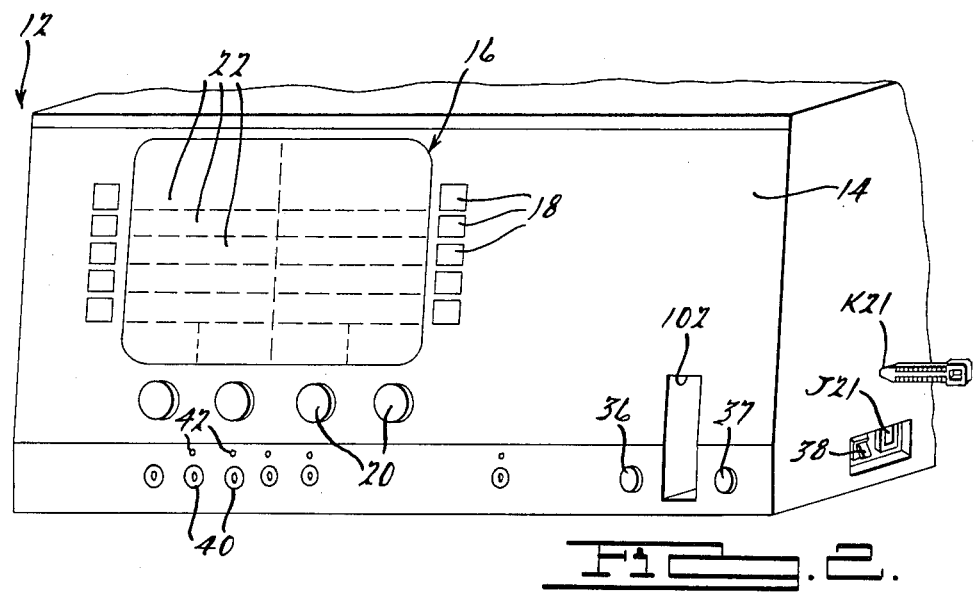
FIG. 2 is a front view of the system console showing the front panel layout in greater detail.

Referring first to FIGS. 1 and 2, a microsurgical control system 10 is provided having a foot pedal assembly 24 according to the present invention. The control system 10 includes a system console 12 which has an upwardly and inwardly sloping front panel 14 and at least one removable access door 254 in one of the side panels. On the front panel 14 is an electronic display screen 16, a plurality of push button switches or touch sensitive pads 18 and a plurality of "endless" digital potentiometer knobs 20. The push buttons 18 and knobs 20 are actuable by the surgeon or nurse to select various different modes of operation and functions used in various surgical procedures.

The console 12 also includes a cassette eject button 36, an irrigation pinch valve 37, and a power on/off switch 38.

The electronic display screen 16 is controlled by a computer to provide one or more different menus or messages which instruct the operator as to the function of the buttons 18 and knobs 20 for the particular mode selected. The display screen 16 may be conceptually divided into display screen regions 22 with the buttons 18 and knobs 20 being positioned at locations around the periphery of the screen 16 corresponding to the regions 22. By virtue of the location of the buttons 18 and knobs 20 adjacent the screen 16, for example, a message in the upper left-hand corner of the screen 16 is readily understood by the operator as referring to the upper left most button. This arrangement allows the indicated function of each button 18 and knob 20 to be readily changed. The use of an electronic display screen 16 also permits the buttons 18 and knobs 20 to be labeled in virtually any language.

The microsurgical control system 10 is adapted for use with a number of different surgical instruments. As shown in FIG. 1, a fiber optic illumination instrument 214 is coupled to the console 12 via fiber optic cable 212. Also illustrated is a fragmentation emulsification instrument 28 coupled to the console 12 through an electrical cable 30. The instrument 28 is also coupled to a collection container or cassette 100 through an aspiration tube 31. A cutting instrument 32 is also shown which is coupled to the console 12 through tubing 34 and to the cassette 100 through tubing 35. The cutting instrument 32 may be a guillotine cutter for vitrectomy procedures, or it may be a microscissors instrument for proportionate and multiple cutting. However, when the microscissors instrument is used, the instrument is not connected to the cassette 100.

While certain microsurgical instruments have been illustrated in FIG. 1, it will be understood that the microsurgical control system 10 can be used with other similarly equipped instruments. In general, any of the microsurgical instruments are actuated or controlled by fluid pressure (positive pressure or negative pressure). However, it should be appreciated that other suitable types of control signals may be used in the appropriate application.

To provide irrigation/aspiration capabilities, the control system 10 further includes the removable cassette 100 which may be inserted into a cassette slot 102 in the console 12. The cassette 100 has a passageway opening 148 to which an aspiration tube from an aspiration instrument may be connected. The console 12 also includes a plurality of couplers 40 to which surgical instruments described above may be attached. Above each coupler 40 is a light emitting diode 42 which is illuminated when the instrument connected to the associated coupler 40 is activated. To store the operating parameters of a particular microsurgical operation, the control system 10 electrically communicates with a digitally encoded memory key K21. The memory key K21 includes an integrated memory circuit which stores the operating parameters for a particular surgical procedure. The console 12 receives the key K21 through a slot J21. Suitable types of memory keys K21 are commercially manufactured by Data Key Inc., Burnsville, Minn. However, it should be appreciated that other suitable means for accessing specifically assigned memory locations may be used in the appropriate application.

A further description of the control system may also be found in the following commonly owned patent applications which were filed on even date herewith, and which are hereby incorporated by reference: Scheller, et al U.S. patent application Ser. No. 928,170, entitled "Control System For Ophthalmic Surgical Instruments"; Scheller, et al U.S. patent application Ser. No. 928,265, entitled "Collection Container For Ophthalmic Surgical System"; and Scheller U.S. patent application Ser. No. 927,807, entitled "Foot Pedal Assembly For Ophthalmic Surgical Instrument".

Figure 3:
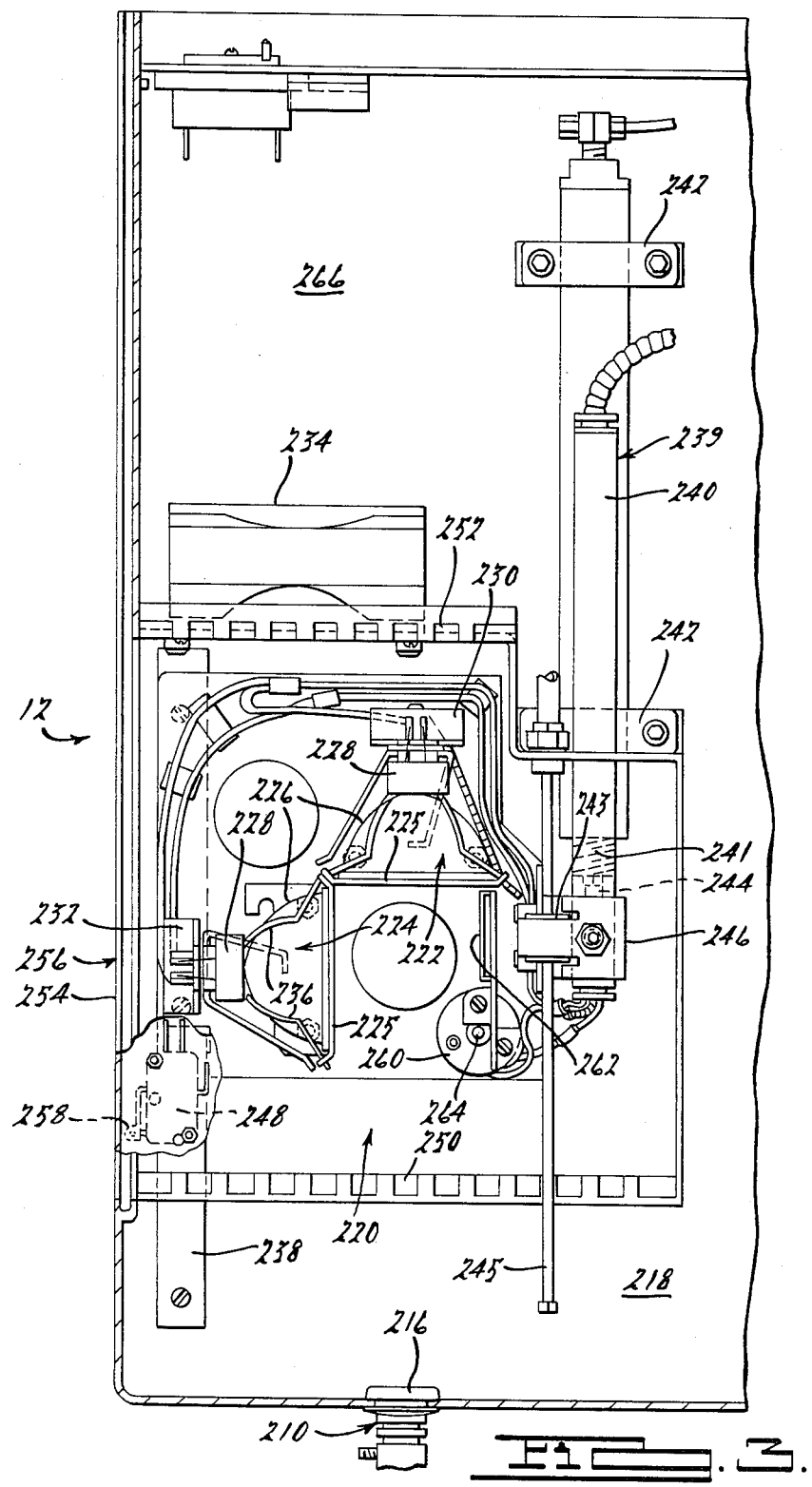
FIG. 3 is a fragmentary cross-sectional view of the console illustrating the illumination system.

With reference to FIGS. 3 and 4, the illumination system will now be described. FIG. 3 illustrates fiber optic coupler 210 as it is installed through the system console wall 12. Coupler 210 has an optical port 216 which is directed inwardly into the interior of the console and which optically communicates with fiber optic cable 212 when the cable is plugged in. Due to the heat generated by this illumination system, the optical coupler 210 may be constructed to provide a heat shield. For example, the optical coupler 210 may include a Teflon (R) sleeve to provide heat insulation.

Secured within the base 218 of the system console 12 is a movable carriage 220 which in turn carries a pair of lamps 222 and 224. Lamps 222 and 224 may be quartz halogen lamps, such as the type used in slide projectors. Lamps 222 and 224 each include an integral parabolic rear reflector 226 for directing the illumination and a base 228 for plugging into sockets 230 and 232 to provide electricity to the lamps. Sockets 230 and 232 are mounted on carriage 220 and are wired to the electrical control circuit discussed below. Lamps 222 and 224 have face plates 225 and are retained in their respective sockets by means of wire holding straps 236.

Carriage 220 is slidably carried on a rail 238 which is secured to the floor of base 218. Rail 238 is preferably fabricated from a self-lubricating plastic material to minimize friction and ensure freedom of movement of the base 218 on the rail. Rail 238 supports the left side of carriage 220. The right side of carriage 220 is supported above base 218 by means of a pneumatic cylinder assembly 239 and block 246. The pneumatic cylinder assembly 239 has a pneumatic cylinder 240 which is secured to base 218 by straps 242. Cylinder 240 has a plunger arm 244 whose position is controlled by valves (not shown) which charge and exhaust the cylinder with the assistance of an internal return spring 241 disposed in the front of the cylinder. A linear pot device 243 is used to provide a feedback signal for determining the position of the plunger arm 244. The linear pot device includes a slider arm 245 which extends in the direction of travel for the plunger arm 244.

The plunger arm 244 of cylinder 240 is connected to the block 246, which is in turn supported by the carriage 220. Carriage 220 is thus permitted to move back and forth in a linear sliding movement toward and away from fiber optic coupler 210. The position of carriage 220 is changed by activation of the pneumatic cylinder assembly 239 to change the intensity of the light entering the optical port 216. This operation is discussed in more detail below. However, it should be appreciated that in the appropriate application, the pneumatic cylinder 240 could be replaced by another suitable means for moving the carriage 220, such as a D.C. servo motor and worm gear arrangement.

To prevent the lamps from overheating, a miniature fan 234 is mounted to the base 218 at the rear of the carriage 220. Base 218 may be provided with upstanding perforated front and rear walls 250 and 252 to permit flow through ventilation for cooling the lamps.

As seen in FIG. 1, the left side of the console is provided with an access door 254 which may be opened to gain access to the lamps. In order to provide a safety interlock, microswitch 248 (FIG. 3) is positioned adjacent the access door opening 256 and includes an actuator arm 258 which senses the open and closed positions of the access door. Microswitch 248 can be connected, for example, to prevent actuation of the electrical circuit and thus prevent actuation of the lamps when the access door is opened.

The illumination system further comprises a means for selectively causing the illumination from either lamp 222 or 224 to illuminate optical port 216. As shown in FIGS. 3 and 4, a rotary solenoid 260 is secured to the carriage 220 and has a mirror assembly 262 coupled to the rotary shaft 264. Rotary solenoid 260 may be energized to selectively move the mirror assembly to a first position shown in solid lines and to a second position shown in dotted lines (FIG. 3). When the rotary solenoid terminal is not energized, the solenoid 260 returns to a spring-biased rest position (preferably shown in solid lines in FIGS. 3 and 4).

In the first position, lamp 222 is in direct line of sight with optical port 216 and can thus illuminate the optical port directly. Lamp 224, if energized, casts a beam generally at right angles to the beam of lamp 222 and thus lamp 224 is not in direct line of sight with optical port 216. When the mirror assembly is rotated to the second position, the mirror is angled approximately 45° so that the illumination from lamp 224 reflects from the mirror and illuminates optical port 216. Preferably, lamp 222 would not be illuminated when the mirror is in the second position. As will be more fully explained below, the rotary solenoid 260 is actuated to rotate from one position to another when one of the lamps (the primary illumination source) burns out. In such event, the other lamp (the auxiliary or secondary illumination source) is energized. It should be appreciated that in the appropriate application, the lamps could be mounted for rotation in place of a rotatable mirror structure.

Referring now to FIG. 5, the electronic lamp driver circuit is illustrated. Preferably, the control circuit is constructed on a printed circuit board for mounting in the space behind the carriage 220, designated generally by reference numeral 266 in FIG. 3. The control circuit is adapted for coupling to the master computer control system circuit on the mother board or analog peripheral device driver board located elsewhere in the system console 12. A jack 268 is provided for this purpose.

Jack 268 comprises a plurality of terminals for providing the following control circuit functions: secondary lamp control, current sensing, emergency power control, SCR gate and voltage sensing. Jack 268 also has terminals for providing both plus and minus 12-volt levels and a terminal for AC return. For a more complete description of the analog peripheral device driver circuitry and the associated computer control system, reference may be had to the above-referenced copending application entitled "Control System For Ophthalmic Surgical Instruments".

The control circuit further includes a power supply jack 270 with terminals for supplying both 18.2-volt RMS and 12.0-volt RMS AC current. As illustrated in FIG. 5, jack 270 uses a pair of redundant terminals for each of the AC voltages as well as a redundant pair of terminals for the AC return. The use of a redundant pair of terminals on jacks and relays is adopted elsewhere in the control circuit, as will be seen by studying the circuit diagram 5. The use of double terminals or double contacts provides an added measure of reliability to the circuit.

The control circuit further comprises a jack 272 to which the primary and secondary lamps and the rotary solenoid are connected. Jack 272 thus provides the power for energizing the lamps and for switching the rotary solenoid as required. Finally, the circuit includes a bipolar power jack 274.

The control circuit comprises an emergency power relay 276 which is activated by a control signal on the emergency power control terminal of jack 268. This relay switches the illumination circuits from the 18.2-volt RMS primary energy source to the 12-volt RMS emergency or auxiliary power source. FIG. 5 illustrates relay 276 in the normal operating position (primary power source). As illustrated, emergency power relay 276 is a four-pole, double-throw relay with the common side of its four poles coupled together at bus 278. Bus 278 is connected to one of the main terminals of triac 280. The other main terminal of triac 280 is coupled to the lamp power bus 282.

The gate terminal of triac 280 is coupled to optoisolator circuit 284 which is in turn responsive to the SCR gate terminal of jack 268. Triac 280 may be implemented using an SC245 device and optoisolator 284 may be implemented using an MCP3010 device. A current sensing resistor 286 is coupled to the lamp power bus and also to the optoisolator 284 for providing the bias current for triac 280 when a gating signal is applied at the SCR gate terminal. When primary power is supplied via the 18.2-volt RMS line, bus 278 is at 18.2 volts. Assuming triac 280 is gated on, the lamp power bus 282 is also at 18.2 volts. If triac 280 is gated off, the lamp power bus 282 is disconnected from primary power. When relay 276 is switched to the auxiliary power position, the 12-volt RMS bus is connected to bus 278. Also, by operation of the relay contacts, bus 278 is connected to the lamp power bus 282. Thus when auxiliary power is being used, triac 280 is bypassed. Regardless of which power source is being used, the voltage sensing terminal of jack 268 is connected to the lamp power bus 282, supplying the power supply voltage information to other parts of the system console circuits.

Lamp power bus 282 is coupled to a Hall effect sensor 288 which measures the current flow through the lamp power bus and provides a signal indicative of the current flow to the current sensing terminal of jack 268. Current flow through lamp power bus 282 indicates that the lamp connected to that bus is not burned out. When the lamp burns out, current will cease to flow in bus 282. Thus the output of Hall effect device 288 gives an indication of the bulb status. This bulb status information is used to determine whether the primary lamp or the secondary lamp is energized and is used to switch the rotary solenoid to the appropriate position. The illumination source relay 290 performs this function.

Illumination source relay 290 is a four-pole, double-throw relay having a first two of its common poles mutually connected to lamp power bus 282 as at 292. When relay 290 is in its normal operating state, the lamp power bus is connected to the primary lamp supply line 294. When relay 290 is switched to the alternate position, lamp power bus 282 is connected to the secondary lamp supply line 296. Relay 290 is switched between the first and second positions by signals on the secondary lamp control terminal of jack 268. Relay 290 has a third pole coupled to the bipolar power source of jack 274. When the rotary solenoid terminal is not energized, the solenoid returns to its spring-biased rest position.

When operating on auxiliary power, diode 298 is used to supply the third pole of relay 290 with power. By properly configuring the system, either lamp 222 or 224 may be set up to serve as the primary light source. Preferably, lamp 222 is the primary lamp. Thus, under normal operating conditions, solenoid 260 is rotated and spring biased to the mirror retracted position shown in solid lines in FIG. 3. Illumination from lamp 222 strikes the optical port 216 and travels through the fiber optic cable 212 to the tip or instrument 214 for illuminating the surgical situs.

If it is desired to change the intensity of the illumination, the surgeon provides the appropriate signal via foot pedal 24 or front system console, which in turn produces a change in the pneumatic pressure within the pneumatic cylinder 240. This causes the plunger arm 244 of pneumatic cylinder 240 to extend or retract, thereby moving carriage 220 to a new position. When the lamp is moved closer to the optical port, the intensity increases; and when it moves further away from the optical port, the intensity decreases. The increase or decrease in intensity is brought about without change in the color temperature of the illumination.

Since the linear pot device 243 provides an "analog" signal which is indicative of the plunger position, the control console circuitry may include an amplifier and A/D converter for interfacing this signal with the data bus of console's master computer control system. This circuitry may also include an I/O register tied to the data bus and a valve driver circuit tied to the output of the I/O register in order to permit the computer to transmit a plunger position command signal from the data bus to the pneumatic valves which control the pneumatic cylinder 240.

If lamp 222 burns out during the operation, Hall effect sensor 288 senses the drop off in current flow through the lamp power bus 282. A signal indicative of this fact is sent back to the master controller circuit of the master computer control system via the current sensing terminal of jack 268. The master computer control circuit interprets this signal as a lamp failure and issues a control signal to the secondary lamp control terminal of jack 268. This signal energizes relay 290, causing the relay to switch lamp power bus 282 to the secondary lamp supply line 296. The secondary lamp 224, being a fresh bulb, draws current through the lamp power bus 282. Hall effect sensor 288 responds to this current flow by returning the current sense terminal to its normal operating state.

At the same time, relay 290 switches power to the rotary solenoid 260, causing the mirror assembly to rotate to the second position, shown in dashed lines in FIG. 3. Illumination from lamp 224, now energized, reflects from the surface of the mirror and onto optical port 216. The optical path length from lamp 222 to the optical port 216 is the same as the optical path length from lamp 224 via mirror 262 to optical port 216. Hence, the intensity of illumination is maintained substantially constant when switching from the primary to the secondary lamp. Lamp 224, like lamp 222, is carried by carriage 220 hence the same control over the intensity of illumination is provided.

In the event of a primary power failure, the master control circuit senses the power failure and sends a control signal to the emergency power control terminal of jack 268. This causes relay 276 to switch from the position shown in FIG. 5 to the alternative position. In the alternate position, the 12-volt RMS bus is connected to bus 278 and also connected to the lamp power bus 282. In this fashion, the lamps and solenoid may be operated using auxiliary power.

When operating from primary power, the lamps may be turned off via triac 280. Triac 280 can also be used as a power controller for varying the duty cycle of the 18-volt RMS power in order to effect lamp dimming without using the movable carriage. This auxiliary means of providing dimming would be used, for example, where a change in color temperature would not be a problem and also used to set the initial intensity of the illumination for subsequent variation by the movable carriage system.

While the invention has been illustrated and described in its presently preferred embodiment, it will be understood that the invention is capable of modification and change without departing from the spirit of the invention as set forth in the appended claims.

What is claimed is:

1. An illumination system for a microsurgical apparatus comprising:
    a base;
    a lamp carriage mounted to said base for movement relative to said base;
    a lamp carried on said lamp carriage for providing illumination;
    a fiber optic coupler disposed on said base for coupling to a fiber optic microsurgical illumination instrument and having a nonfocusing optical port positioned to receive said illumination from said lamp; and
    means coupled to said carriage for moving said carriage selectively toward and away from said coupler to change the intensity of the illumination entering said optical port without substantially changing the focus of said illumination entering said optical port.

2. The illumination system of claim 1 wherein said lamp provides a substantially constant color temperature illumination.

3. The illumination system of claim 1 wherein said means for moving said carriage comprises a pneumatic means coupled to said carriage.

4. The illumination system of claim 3 wherein said pneumatic means confines movement of said carriage to linear movement.

5. The illumination system of claim 1 further comprising a second lamp carried on said lamp carriage for providing auxiliary illumination.

6. The illumination system of claim 5 further comprising illumination directing means on said carriage for selectively directing illumination from either said lamp or said second lamp to said coupler.

7. The illumination system of claim 5 further comprising mirror means for directing the illumination from at least one of said lamps to said coupler.

8. The illumination system of claim 7 wherein said mirror means is movable from a first position whereby said lamp illuminates said coupler to a second position whereby said second lamp illuminates said coupler.

9. The illumination system of claim 8 further comprising remotely actuable means for effecting movement of said mirror means from said first position to said second position.

10. An illumination system for a microsurgical apparatus comprising:
a base;
a fiber optic coupler disposed on said base for coupling to a fiber optic microsurgical illumination instrument and having a nonfocusing optical port;
at least two lamps supported on said base each for providing illumination;
illumination controlling means supported on said base for selectively causing the illumination from either of said lamps to illuminate said optical port;
carriage means movably mounted to said base, said two lamps and said illumination controlling means being mounted on said carriage means; and
means coupled to said carriage means for moving said carriage means selectively toward and away from said coupler to change the intensity of the illumination entering said optical port without substantially changing the focus of said illumination entering said optical port.

11. The illumination system of claim 10 wherein said lamps each provide a substantially constant color temperature illumination.

12. The illumination system of claim 10 wherein said illumination controlling means comprises an illumination directing means for selectively directing the illumination from either of said lamps onto said optical port.

13. The illumination system of claim 10 further comprising sensing means coupled to said controlling means for sensing when a first of said lamps is not providing illumination and for automatically causing said controlling means to cause a second of said lamps to illuminate said optical port.

14. The illumination system of claim 13 wherein said sensing means comprises means for sensing electrical current flow through said first of said lamps.

15. The illumination system of claim 13 wherein said sensing means comprises Hall effect means for sensing electrical current flow through said first of said lamps.

16. The illumination system of claim 10 wherein said controlling means comprises mirror means for directing illumination from at least one of said lamps onto said optical port.

17. The illumination system of claim 10 wherein said controlling means comprises mirror means carried on said base and movable from a first position whereby a first one of said lamps illuminates said optical port to a second position whereby a second one of said lamps illuminates said optical port.

18. The illumination system of claim 10 further comprising a primary means for supplying electrical current to said lamps and an auxiliary means for supplying electrical current to said lamps operable in the event of failure of said primary means.

19. The illumination system of claim 10 wherein said lamps include integral rear reflector means for controlling the direction of illumination.

20. The illumination system of claim 10 wherein said two lamps are positioned such that the optical path lengths from said two lamps to said optical port are substantially the same.

* * * * *